United States Patent [19]

Alexander et al.

[11] 4,391,806

[45] Jul. 5, 1983

[54] SUBSTITUTED TETRAHYDROPYRIDAZINO-(1,6-A)BENZIMIDAZOLES AND USE AS BRONCHODILATORS

[75] Inventors: Catherine A. Alexander, Indianapolis; Robert J. Cregge, Zionsville; Norton P. Peet, Indianapolis, all of Ind.

[73] Assignee: The Dow Chemical Company, Midland, Mich.

[21] Appl. No.: 397,300

[22] Filed: Jul. 12, 1982

[51] Int. Cl.³ ............... A61K 31/535; A61K 31/50; C07D 487/04

[52] U.S. Cl. .................. 424/248.4; 424/43; 424/250; 544/115; 544/234; 260/243.3

[58] Field of Search ............... 544/115, 234; 260/243.3; 424/248.4, 250, 43

[56] References Cited

U.S. PATENT DOCUMENTS 4,166,851  9/1979  Baldwin et al. ............... 424/248.55
4,233,301  11/1980  Baldwin et al. ............... 424/250

*Primary Examiner*—Robert W. Ramsuer
*Attorney, Agent, or Firm*—John J. Kolano; Gary D. Street; Raymond A. McDonald

[57] ABSTRACT

Substituted tetrahydropyridazino[1,6-a]benzimidazole compounds such as 2-methylamino-6,7,8,9-tetrahydropyridazino[1,6-a]benzimidazole are prepared by reacting a 2-halo-6,7,8,9-tetrahydropyridazino[1,6-a]benzimidazole with an appropriate amine. The compounds are useful as bronchodilators.

5 Claims, No Drawings

SUBSTITUTED TETRAHYDROPYRIDAZINO-(1,6-A)BENZIMIDAZOLES AND USE AS BRONCHODILATORS

The present invention relates to tetrahydropyridazino[1,6-a]benzimidazoles having an amino substitutent at the 2-position. More particularly, it relates to compounds having the following general formula:

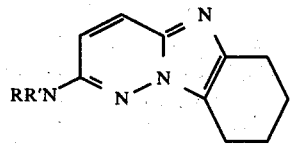

wherein —NRR' is (lower alkyl)amino, (lower alkyl)-2—amino, 1-pyrrolidinyl, 1-piperidinyl, methyl-1-piperidinyl, hexahydroazepin-1-yl, 4-methyl-1-piperazinyl, 4-methylhexahydro-1,4-diazepin-1-yl and 4-morpholinyl. The present invention further encompasses the pharmaceutically acceptable acid addition salts of the aforesaid amino compounds.

The lower alkyl groups referred to above contain 1 to 6 carbon atoms and can be exemplified by groups such as, methyl, ethyl, propyl, isopropyl, butyl, and hexyl.

Acid addition salts of the aforesaid compounds with pharmaceutically acceptable acids are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid.

Examples of compounds encompassed by the present invention are the following:
- 2-Methylamino-6,7,8,9-tetrahydropyridazino[1,6-a]benzimidazole.
- 2-Dimethylaminop-6,7,8,9-tetrahydropyridazino[1,6-a]benzimidazole.
- 2-Diethylamino-6,7,8,9-tetrahydropyridazino[1,6-a]benzimidazole.
- 2-(Hexahydroazepin-1-yl)-6,7,8,9-tetrahydropyridazino[1,6-a]benzimidazole.
- 2-(4-Methyl-1-piperazinyl)-6,7,8,9-tetrahydropyridazino[1,6-a]benzimidazole.

The substituted tetrahydropyridazino[1,6-a]benzimidazole compounds as described above are bronchodilators and are thus useful for the treatment of bronchial disorders such as bronchial asthma. The present invention is further directed to a method of effecting bronchodilation.

In practicing the method of this invention, an effective bronchodilating amount of 1 or more substituted tetrahydropyridazino[1,6-a]benzimidazoles of this invention is administered internally to a mammal in need thereof by a route effective to bring the compound into contact with the bronchial and tracheal tissues of the mammal. Administration can be carried out either by a parenteral route, such as by intravenous, intraperitoneal or intramuscular injection, or by introduction into the gastrointestinal tract via oral or rectal administration, for example, in order to bring about such contact via the blood stream, or by intratracheal administration, by inhalation of a solution in the form of a spray, for example.

The effective bronchodilating amount of the compound, that is, the amount sufficient to inhibit or alleviate bronchial spasm, depends on various factors such as the size, type and age of the animal to be treated, the particular compound or pharmacologically-acceptable salt employed, the route and frequency of administration, the severity of any spasm and the causative agent involved, and the time of administration. In particular cases, the dosage to be administered can be ascertained by conventional range finding techniques, for example, by observing the bronchodilator activity produced at different dosage rates. More specifically, the compounds can be administered at dosage rates ranging from about 1 to about 100 milligrams of substituted tetrahydropyridazino[1,6-a]benzimidazole compound per kilogram of animal body weight with other ranges being from about 1 to about 10 of from 1 to about 3 milligrams per kilogram. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are generally preferred and the active compound can be formulated in conventional time release capsule or tablet formulations although injectable compositions or sprays and aerosols for inhalation are preferred when rapid action is desired.

In practicing the method of this invention, the active ingredient is preferably incorporated in a composition comprising a pharmaceutical carrier and from about 5 to about 90 percent by weight of the substituted tetrahydropyridazino[1,6-a]benzimidazole compound or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions and solutions for sprays, and can contain suitable excipients known to be useful in the preparation of the particular type of composition desired. Suitable pharmaceutical carriers and formulation techniques are found in standard texts, such as Remington's Pharmaceutical Sciences, Mack Publishing Company, Easton, Pa.

In evaluating bronchodilator activity, test compounds were administered to guinea pigs by intraperitoneal injection or orally and the guinea pigs were challenged by exposure to a histamine aerosol at periods ranging from 30 minutes to 4 hours later. Untreated animals collapsed when exposed to the histamine aerosol. In the operations, the animals were observed and collapse times were recorded. The collapse times observed were then compared statistically with control animals treated with water alone with the control group usually being a long-term cumulative control. When tested by the above procedure, the compounds of the present invention were found to produce a bronchodilating effect.

The compounds of the present invention are conveniently prepared by the reaction of a 2-halo-6,7,8,9-tetrahydropyridazino[1,6-a]benzimidazole with an appropriate amine. The 6-halo substituent is preferably chlorine although it can also be bromine. This 2-halo compound is reacted with an excess of the amine in an inert solvent. More specifically, the reaction is carried out at the boiling temperature under reflux or at about 60° C. to 110° C. using an excess of the base or an inert organic solvent such as methanol, ethanol or 2-propanol as a medium. The product is recovered by conventional procedures such as concentration under reduced pressure.

The necessary starting material referred to above is obtained by the reaction of 3-amino-6-chloropyridazine with 2-chlorocyclohexanone in a solvent such as ethanol. The desired halo-tricyclic compound is obtained directly by this reaction.

The following examples are presented to illustrate the present invention but they should not be construed as limiting it in any way.

EXAMPLE 1

To a solution of 5.0 g of 3-amino-6-chloropyridazine in 75 ml of ethanol was added 10.1 g of 2-chlorocyclohexanone. The resulting solution was stirred and heated at reflux for 48 hours and then excess ethanol was evaporated under reduced pressure. This gave a tan oily residue which solidified upon trituration with toluene. The solid was separated by filtration but it again became oily and appeared to be hygroscopic. The product obtained in this way was 2-chloro-6,7,8,9-tetrahydropyridazino[1,6-a]benzimidazole.

EXAMPLE 2

A mixture was prepared from 5.0 g of 2-chloro-6,7,8,9-tetrahydropyridazino[1,6-a]benzimidazole and 30 ml of pyrrolidine and this was stirred and heated at reflux for 18 hours. The reaction mixture was then poured into 200 ml of ice water. A solid formed and this was separated by filtration and recrystallized from a mixture of ethanol and water to give 2-(1-pyrrolidinyl)-6,7,8,9-tetrahydropyridazino[1,6-a]benzimidazole melting at about 161° C. This compound has the following structure formula

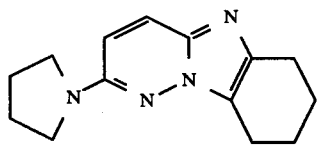

EXAMPLE 3

A mixture was prepared by adding 5.0 g of 2-chloro-6,7,8,9-tetrahydropyridazino[1,6-a]benzimidazole to 30 ml of morpholine and this was stirred and heated at reflux for 24 hours. It was then poured into 200 ml of ice water. A tan solid formed and this was separated by filtration to give 2-(4-morpholinyl)-6,7,8,9-tetrahydropyridazino[1,6-a]benzimidazole melting at 187.5°-188.5° C.

EXAMPLE 4

A solution of 5.0 g of 2-chloro-6,7,8,9-tetrahydropyridazino[1,6-a]benzimidazole in 30 ml of piperidine was stirred and heated at reflux for 72 hours. The reaction mixture was poured into 200 ml of ice water and the tan solid which formed was separated by filtration and air dried. It was then recrystallized from a mixture of ethanol and water to give 2-(1-piperidinyl)-6,7,8,9-tetrahydropyridazino[1,6-a]benzimidazole melting at about 184°-185° C.

EXAMPLE 5

A mixture was prepared from 5.0 g of 2-chloro-6,7,8,9-tetrahydropyridazino[1,6-a]benzimidazole and 30 ml of 1-methylhomopiperazine and this was stirred and heated at reflux for 18 hours. The reaction mixture was then cooled and excess amine was removed by distillation to leave a tan solid residue. This solid was partitioned between methylene chloride and an aqueous 1% solution of sodium hydroxide. The methylene chloride layer was separated and the solvent was evaporated under reduced pressure to leave a residual solid. This solid was recrystallized from a mixture of ethanol and water to give 2-(4-methyl-1-homopiperazinyl)-6,7,8,9-tetrahydropyridazino[1,6-a]benzimidazole melting at about 106°-107° C.

EXAMPLE 6

A mixture of 5.0 g of 2-chloro-6,7,8,9-tetrahydropyridazino[1,6-a]benzimidazole in 30 ml of 4-methylpiperidine was stirred and heated at reflux for 24 hours. The reaction mixture was then poured into 200 ml of ice water, a tan solid formed, and this was separated by filtration. The solid was then recrystallized from a mixture of ethanol and water to give 2-(4-methyl-1-piperidinyl)-6,7,8,9-tetrahydropyridazino[1,6a]benzimidazole melting at about 139°-141° C. This compound has the following structural formula

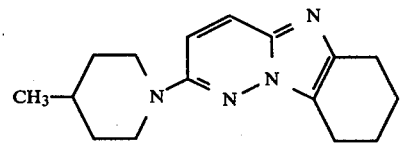

What is claimed is:
1. A compound of the formula:

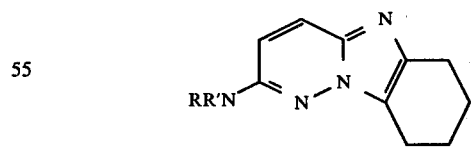

wherein —NRR' is (lower alkyl)amino, di(lower alkyl)amino, 1-pyrrolidinyl, 1-piperidinyl, methyl-1-piperidinyl, hexahydroazepin-1-yl, 4-methyl-1-piperazinyl, 4-methylhexahydro-1,4-diazepin-1-yl and 4-morpholinyl; and the pharmaceutically acceptable acid addition salts of said compound.

2. A compound according to claim 1 which is 2-(1-pyrrolidinyl)-6,7,8,9-tetrahydropyridazino[1,6-a]benzimidazole.

3. A compound according to claim 1 which is 2-(4-methyl-1-piperidinyl)-6,7,8,9-tetrahydropyridazino[1,6-a]benzimidazole.

4. A compound according to claim 1 which is 2-(4-morpholinyl)-6,7,8,9-tetrahydropyridazino[1,6-a]benzimidazole.

5. A method of producing bronchodilation which comprises administering to a mammal in need thereof an effective amount of a compound of the formula

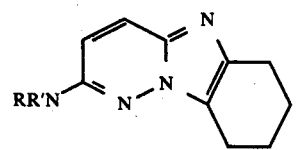

wherein —NRR' is (lower alkyl)amino, di(lower alkyl)amino, 1-pyrrolidinyl, 1-piperidinyl, methyl-1-piperidinyl, hexahydroazepin-1-yl, 4-methyl-1-piperazinyl, 4-methylhexahydro-1,4-diazepin-1-yl and 4-morpholinyl; and the pharmaceutically acceptable acid addition salts of said compound.

* * * * *